United States Patent
Rothstein et al.

(10) Patent No.: US 11,071,533 B2
(45) Date of Patent: Jul. 27, 2021

(54) PERCUTANEOUS ATRIAL AND VENTRICULAR SEPTAL DEFECT CLOSURE DEVICE

(71) Applicant: Medtronic, Inc., Minneapolis, MN (US)

(72) Inventors: Paul Rothstein, Elk River, MN (US); Paul A. Iaizzo, White Bear Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 940 days.

(21) Appl. No.: 15/249,994

(22) Filed: Aug. 29, 2016

(65) Prior Publication Data
US 2017/0049425 A1    Feb. 23, 2017

Related U.S. Application Data

(63) Continuation of application No. 13/614,592, filed on Sep. 13, 2012, now Pat. No. 9,445,797.

(51) Int. Cl.
*A61B 17/00* (2006.01)

(52) U.S. Cl.
CPC .............. *A61B 17/0057* (2013.01); *A61B 2017/00575* (2013.01); *A61B 2017/00584* (2013.01); *A61B 2017/00592* (2013.01); *A61B 2017/00597* (2013.01); *A61B 2017/00606* (2013.01);
(Continued)

(58) Field of Classification Search
CPC ...... A61B 17/0057; A61B 2017/00584; A61B 2017/00597; A61B 2017/00575; A61B 2017/00867; A61B 2017/00606; A61B 2017/00623; A61B 2017/00592
See application file for complete search history.

(56) References Cited

U.S. PATENT DOCUMENTS

| | | | |
|---|---|---|---|
| 5,702,421 | A | 12/1997 | Schneidt |
| 7,905,901 | B2 | 3/2011 | Corcoran |

(Continued)

FOREIGN PATENT DOCUMENTS

| | | |
|---|---|---|
| WO | WO01/049213 | 7/2001 |
| WO | WO03/049619 | 6/2003 |

OTHER PUBLICATIONS

Merriam-Webster definition of "loop" accessed Apr. 9, 2019 (Year: 2019).*

*Primary Examiner* — Tan-Uyen T Ho
*Assistant Examiner* — Rachel S Highland

(57) ABSTRACT

Medical devices for closing anatomical apertures, such as atrial or ventricular septal defects, are disclosed. The medical devices can include a plug body having a proximal end, a distal end, and a longitudinal axis. The plug body can include an exterior surface, an interior surface defining an interior lumen, and a seal which can be located within the interior lumen. The medical devices can also include at least one arm member extending through the plug body between the exterior surface and the interior surface of the plug body. In certain embodiments, the medical device can include a distal loop and a proximal loop extending through the plug body. In certain embodiments, the proximal loop can be smaller than the distal loop, such that a top end and a bottom end of the proximal loop can fit within a top end and a bottom end of the distal loop.

19 Claims, 15 Drawing Sheets

(52) U.S. Cl.
CPC ............... *A61B 2017/00623* (2013.01); *A61B 2017/00867* (2013.01)

(56) References Cited

U.S. PATENT DOCUMENTS

| | | | |
|---|---|---|---|
| 8,951,223 B2* | 2/2015 | McNamara | A61M 27/002 604/8 |
| 9,681,948 B2* | 6/2017 | Levi | A61B 17/0057 |
| 2002/0173742 A1 | 11/2002 | Keren et al. | |
| 2003/0225421 A1 | 12/2003 | Peavey | |
| 2004/0073242 A1 | 4/2004 | Chanduszko | |
| 2004/0176799 A1 | 9/2004 | Chanduszko | |
| 2005/0070957 A1 | 3/2005 | Das Gladwin | |
| 2005/0187564 A1* | 8/2005 | Jayaraman | A61B 17/12022 606/141 |
| 2005/0288786 A1 | 12/2005 | Chanduszko | |
| 2007/0021778 A1 | 1/2007 | Carly | |
| 2007/0073337 A1 | 3/2007 | Abbott et al. | |
| 2007/0250081 A1 | 10/2007 | Cahill | |
| 2007/0282430 A1* | 12/2007 | Thommen | A61B 17/0057 623/1.22 |
| 2008/0065149 A1* | 3/2008 | Thielen | A61B 17/0057 606/213 |
| 2009/0204133 A1 | 8/2009 | Melzer | |
| 2010/0030246 A1* | 2/2010 | Pavcnik | A61B 17/0057 606/157 |
| 2011/0184439 A1* | 7/2011 | Anderson | A61B 17/0057 606/151 |
| 2011/0213410 A1 | 9/2011 | Ginn | |
| 2011/0295362 A1* | 12/2011 | Finch | A61B 17/0057 623/1.26 |
| 2012/0083832 A1* | 4/2012 | Delaloye | A61B 17/0057 606/213 |
| 2013/0178783 A1* | 7/2013 | McNamara | A61F 2/2418 604/9 |

\* cited by examiner

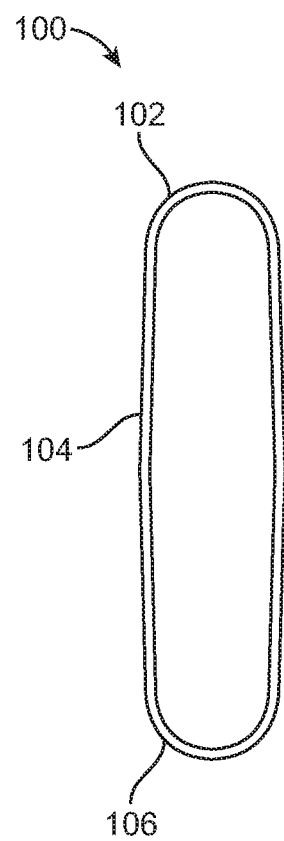 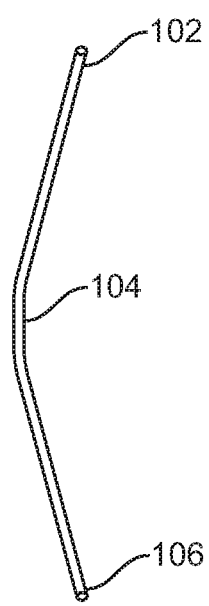 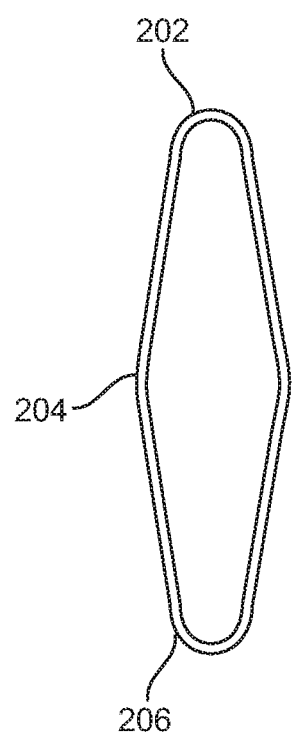 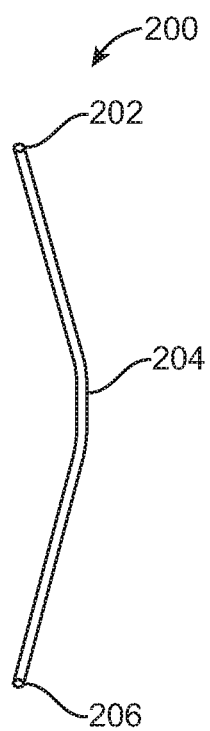
Front View  Side View  Front View  Side View
FIG. 1A  FIG. 1B

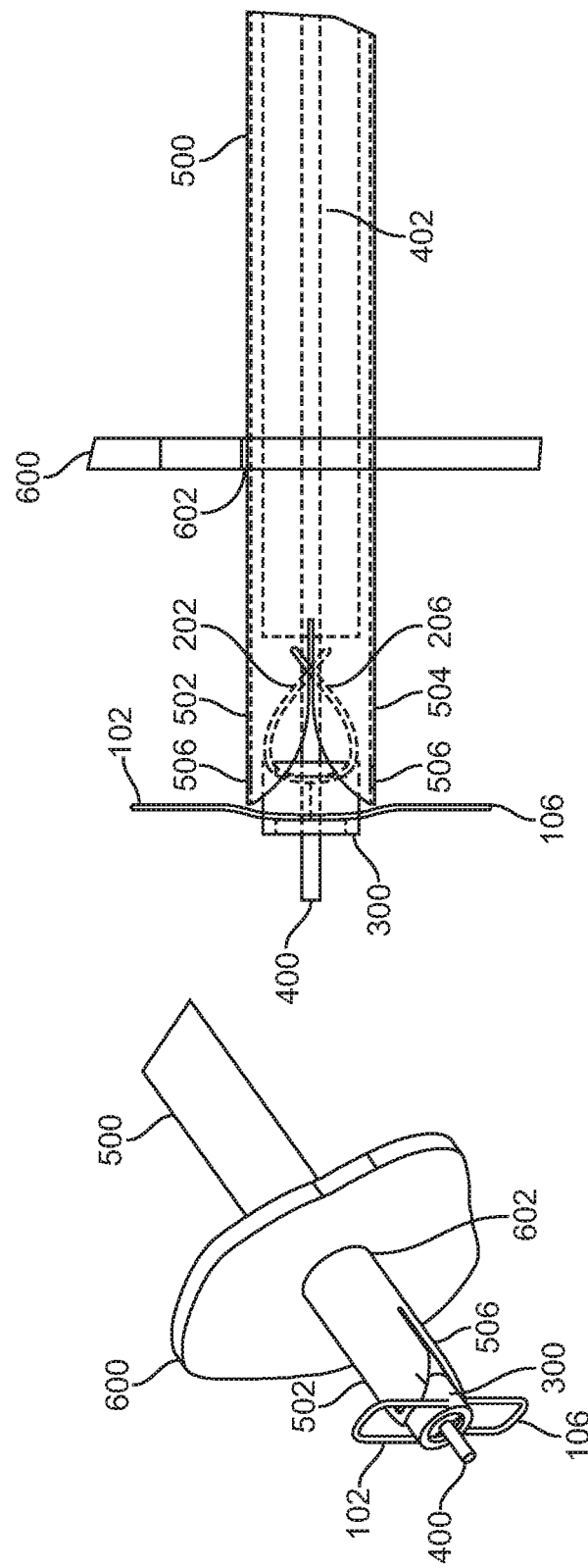

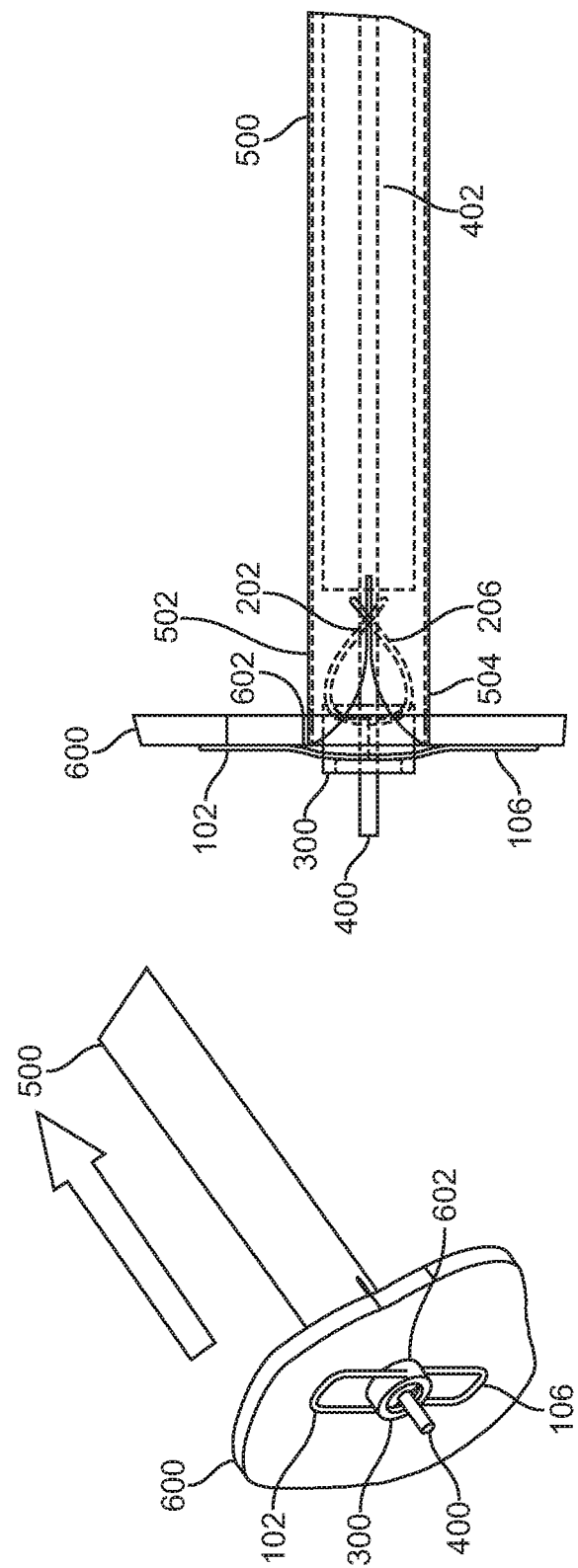

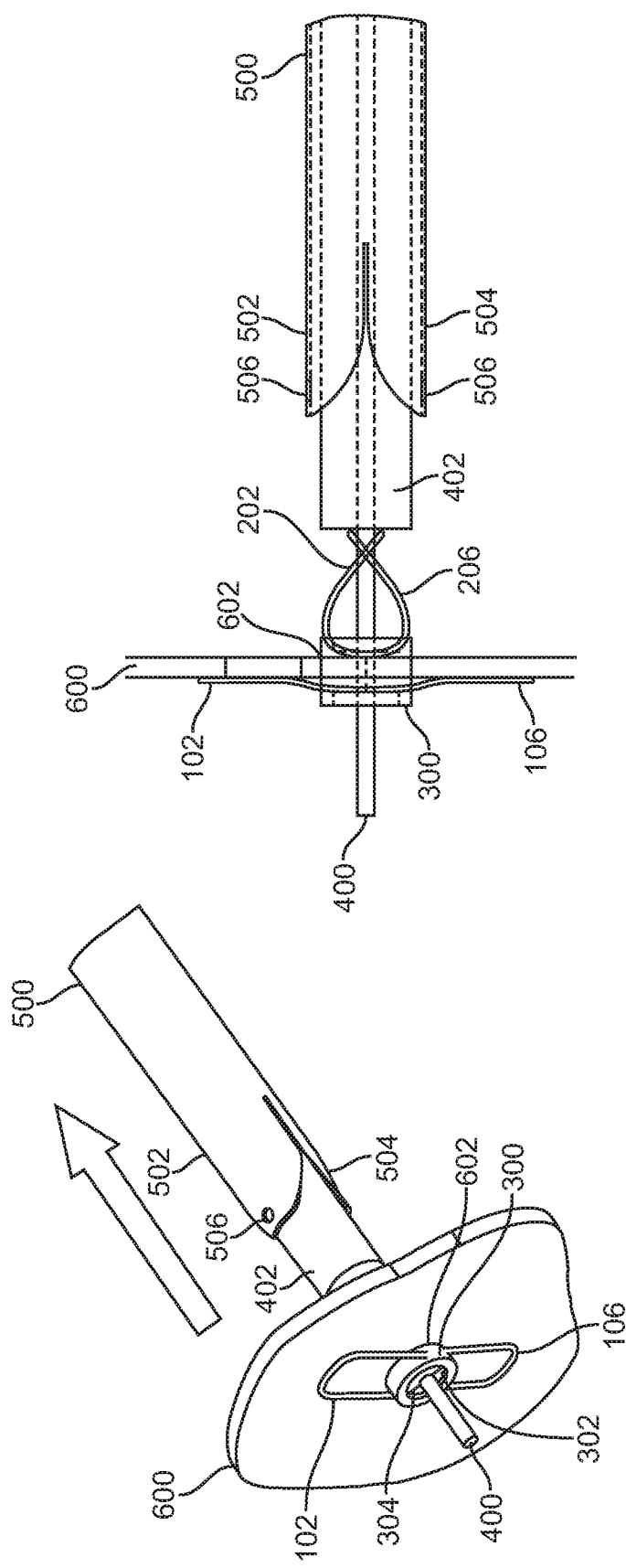

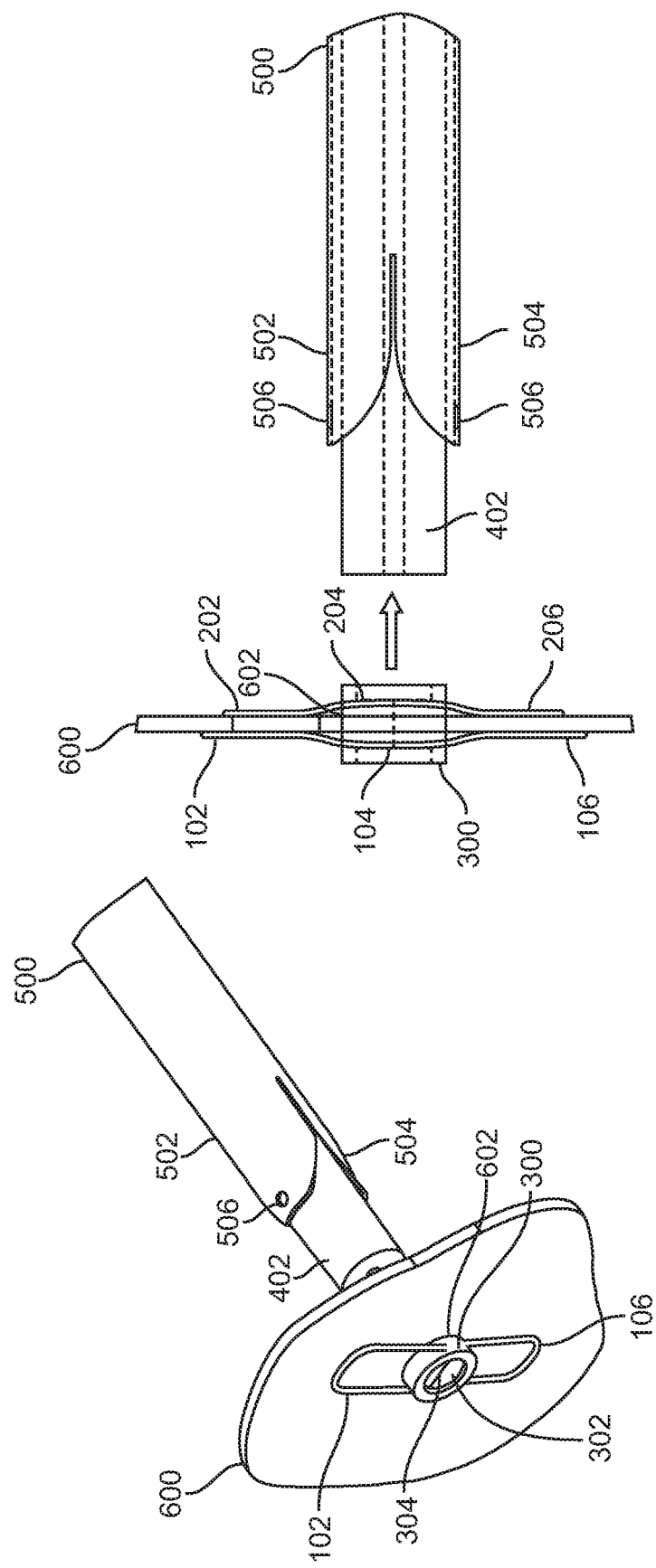

PERCUTANEOUS ATRIAL AND VENTRICULAR SEPTAL DEFECT CLOSURE DEVICE

RELATED APPLICATIONS

This application is a Continuation of and claims the benefit of U.S. patent application Ser. No. 13/614,592 filed Sep. 13, 2012, now allowed. The disclosures of which are herein incorporated by reference in their entirety.

BACKGROUND

Field

The present disclosure relates to medical devices for closing anatomical apertures. More specifically, the present disclosure relates to medical devices for closing atrial and ventricular septal defects and methods of delivering and implanting such medical devices. In certain embodiments, the medical devices disclosed herein can include a plug body and at least one arm member, such as a loop, extending through the plug body between an exterior surface and an interior surface of the plug body. In certain embodiments a seal located within an interior lumen of the plug body can permit one-way access through the medical device.

Background

Atrial Septal Defect (ASD) is a fairly common congenital heart defect, where an opening in the septum separating the left and right atria fails to close after birth. As a result, oxygenated blood can flow from the left atrium into the right atrium, where it mixes with deoxygenated blood and is pumped back into the lungs.

Small ASD generally cause few problems, however, larger ASD can cause health issues, particularly later in life, as the increased blood volume into the right atrium can enlarge and weaken the right atrium and overwork the lungs. Health issues can include frequent respiratory infections, heart palpitations and shortness of breath during activity.

Typically, surgical procedures are successful at correcting ASD. In some instances, open-heart surgery is required, and the patient is placed under general anesthesia and on cardiopulmonary bypass while a surgeon stiches or patches the ASD. Cardiac catheterization is another technique that can be used, whereby a catheter is inserted into a blood vessel, such as the femoral artery, and guided through the patient's vasculature to the heart. The ASD can then be closed, for example, by inserting a plug. Alternatively, a mesh patch can be inserted, over which heart tissue can grow to seal the ASD.

In addition to ASD, an opening is sometimes created between the right atrium and left atrium for percutaneous access to the left side of the heart such as for mitrel valve repair or for catheter ablation for the treatment of atrial fibrillation (AF). The medical devices disclosed herein can close both anatomical defects and surgically created openings. Generally, current percutaneous ASD closure devices require a relatively large and circular landing zone. The medical devices described herein can have a linear landing zone, which can allow the medical device to be implanted in more locations.

BRIEF SUMMARY

The present disclosure relates to medical devices for closing anatomical apertures, such as, but not limited to, atrial or ventricular septal defects. For example, the disclosed medical devices can also be used to close a patent foramen ovale (PFO) or an opening created between the right atrium and left atrium for percutaneous access to the left side of the heart, such as for mitrel valve repair.

The medical devices disclosed can include a plug body having a proximal end, a distal end, and a longitudinal axis. The plug body can include an exterior surface, an interior surface defining an interior lumen, and a seal which can be located within the interior lumen. The medical devices can also include at least one arm member extending through the plug body between the exterior surface and the interior surface of the plug body. In certain embodiments, the at least one arm member can be a loop which extends through the plug body, or a wire resembling a loop with a portion of the loop missing. Generally, the term "loop" will be used throughout the disclosure, however, the term is inclusive of any such arm member extending through the plug body.

In certain embodiments, the medical device can include a distal loop extending through the plug body and a proximal loop extending through the plug body. In certain embodiments, the distal and proximal loops can be oriented generally perpendicular to the longitudinal axis of the plug body. In certain embodiments, the proximal loop can be smaller than the distal loop, such that a top end and a bottom end of the proximal loop can fit within a top end and a bottom end of the distal loop when the proximal and distal loops are assembled with the plug body.

In certain embodiments, the seal located within the interior lumen of the plug body can permit one-way access through the medical device. The medical devices can also employ a hemostatic seal that can be implanted after an opening is created but before insertion of the treatment catheter with the intent of dispersing the force from crossing the septum to a larger area. If desired, the seal can be coated with a cytostatic agent to prevent tissue growth over the seal and to allow re-access to the left atrium at a later time.

Delivery systems for delivering the medical devices described herein are also disclosed. The delivery systems can include a guide wire and a pushing tube, having an interior lumen sized to fit about the guide wire, for pushing the medical device along the guide wire. In certain embodiments, the delivery system can also include a retaining tube sized to fit about the guide wire onto which the medical device can be loaded. In certain embodiments, the delivery system can include a sheath to cover the medical device. In certain embodiments, the sheath can have a distal end including an upper leaf and a lower leaf. Each leaf can have an aperture through which the guide wire can pass to close the distal end of the sheath.

Methods of delivering a medical device and closing an anatomical aperture are also disclosed. Delivery systems carrying medical devices such as the ones disclosed herein can be inserted into a body lumen, and advanced along a guide wire through the body lumen to a deployment location. In certain embodiments, the medical device can be pushed along the guide wire with a pushing tube until the medical device reaches the deployment location. The medical device can then be deployed, for example, by retracting the guide wire in a proximal direction or pushing the medical device in a distal direction off of the guide wire to release the loops from the guide wire.

BRIEF DESCRIPTION OF THE DRAWINGS/FIGURES

FIGS. 1A and 1B illustrate distal and proximal loops detached from the medical device.

FIGS. 8A through 8L illustrate the delivery and deployment sequence for closing an anatomical aperture, according to an embodiment.

DETAILED DESCRIPTION

Figure 2C:
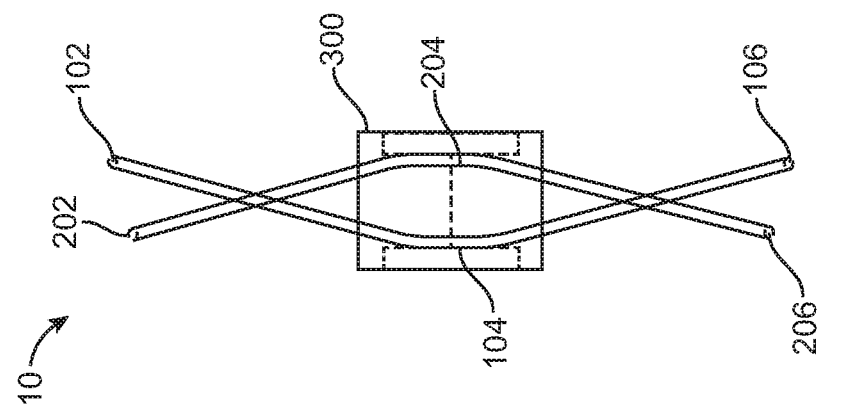
FIGS. 2A through 2O illustrate the medical device, according to an embodiment.

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In certain embodiments, the medical devices disclosed herein for closing an anatomical aperture can include a plug body having a proximal end, a distal end, and a longitudinal axis. The plug body can have an exterior surface and an interior surface defining an interior lumen. A seal can be located within the interior lumen. The medical device can also include at least one loop extending through the plug body between the exterior surface and the interior surface of the plug body.

In certain embodiments, the medical device can include a distal loop and a proximal loop, both of which can extend through the plug body. The distal and proximal loops can be oriented generally perpendicular to the longitudinal axis of the plug body. In certain embodiments, the proximal loop can be smaller than the distal loop, such that a top end and a bottom end of the proximal loop can fit within a top end and a bottom end of the distal loop when the proximal and distal loops are assembled with the plug body. Similarly, in certain embodiments, the distal loop can be smaller than the proximal loop.

In addition, in certain embodiments, delivery systems for delivering the medical devices disclosed herein can include a guide wire and a pushing tube having an interior lumen sized to fit about the guide wire. The pushing tube can push the medical device along the guide wire to the deployment location. In certain embodiments, a sheath can cover the medical device as it is pushed along the guide wire.

FIGS. 1A and 1B illustrate distal loop 100 and proximal loop 200, respectively, of closure device 10, including front and side views. Distal loop 100 can include top end 102, middle portion 104 and bottom end 106. Similarly, proximal loop 200 can include top end 202, middle portion 204, and bottom end 206.

In certain embodiments, distal loop 100 and proximal loop 200 can be made of a shape-memory alloy, for example, nitinol. In certain embodiments, the loops can be made of other materials with elastic properties. The loops can be biased to a preset shape, such that the loops can return to the preset shape after being delivered in a delivery configuration.

Generally, distal loop 100 and proximal loop 200 can be oriented perpendicular to the longitudinal axis of plug 300. In certain embodiments, distal loop 100 can be larger than proximal loop 200 such that top end 202 and bottom end 206 of proximal loop 200 can pass through top end 102 and bottom end 106 of distal loop 100 when assembled with plug 300. In certain embodiments, top end 102 and bottom end 106 of distal loop 100 can be angled toward the proximal end of plug 300, and top end 202 and bottom end 206 of proximal loop 200 can be angled toward the distal end of plug 300. This configuration can create a larger spring force from the loop ends towards the tissue plane when closure device 10 is deployed within the anatomical aperture. In certain embodiments, top end 202 of proximal loop 200 can cross under top end 102 of distal loop 100, and bottom end 206 of proximal loop 200 can cross over bottom end 106 of distal loop 100, when the loops are in a closed configuration.

Figure 3:
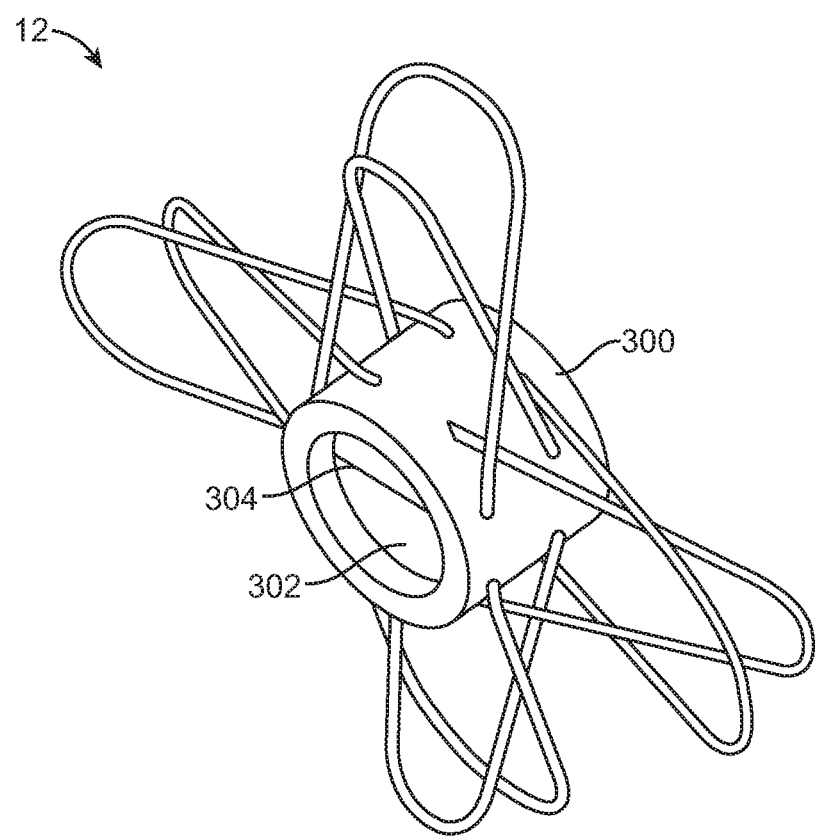
FIG. 3 illustrates an alternative embodiment of the medical device.

As illustrated in FIG. 3, the medical device can include multiple loops. Closure device 12, shown in FIG. 3, includes four loops, which when inserted through plug 300 create eight distinct loop sections protruding from plug 300. Alternatively, a single loop design can have a large loop on one end and a small loop on another end, where the two loops are mounted in opposite orientation to each other. Various numbers of loops, loop sizes, and loop patterns can be used to create different loop configurations. Additionally, as discussed above, alternative forms of arm members extending through the plug body can be used.

Figure 2B:
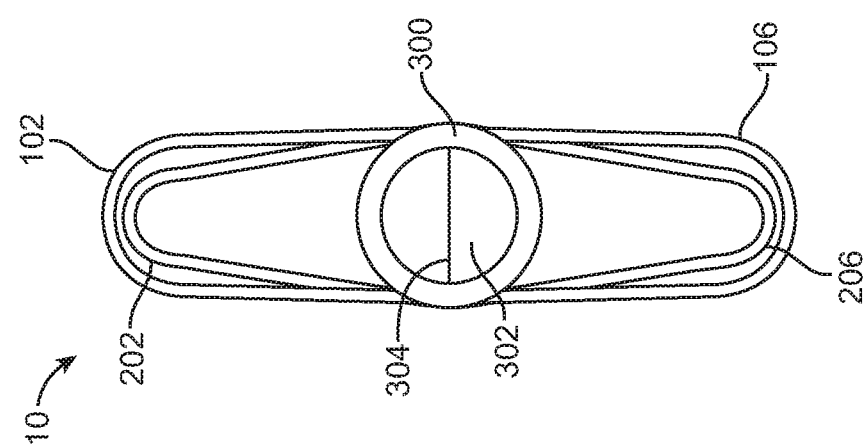
Figure 2A:
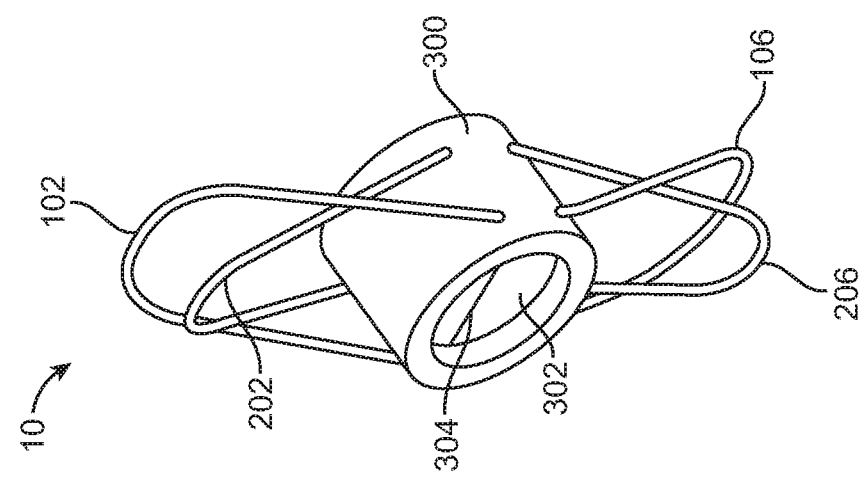

FIGS. 2A through 2C illustrate closure device 10 with distal loop 100 and proximal loop 200. Distal loop 100 and proximal loop 200 can extend through plug 300 such that middle portions 104 and 204 extend between an interior and exterior surface of plug 300. In certain embodiments, plug 300 can be cylindrical in shape, although other shapes, e.g., diamond, square, ellipsoid, etc., can be used. In certain embodiments, plug 300 can be made of a rigid or semi-rigid material, such as plastic, that can encase or otherwise provide a landing for permanent fixation of middle portions 104 and 204. In certain embodiments, the size of plug 300 can be approximately 4.5 millimeters in diameter. However, it should be understood that any range of sizes and shapes can be used to close different sized anatomical apertures.

Seal 302 can be located within an interior of plug 300. Seal 302 can be made of a soft compressible material and, in certain embodiments, can have slit 304 in its center. Slit 304 can allow items slightly smaller than the inside diameter of plug 300 to pass through, but can reseal once the item is removed. Other sealing methods can be employed, such as, but not limited to, one-way seals and duck-billed seals. In certain embodiments, seal 302 and slit 304 can be made from a single, molded piece of material, for example, silicone polymer. In certain embodiments, seal 302 can be a pierceable septum. Seal 302 can allow a medical tool, such as a catheter, to pierce seal 302 and then self-reseal once the medical tool is removed. In certain embodiments, portions of closure device 10 can be coated or infused with a cytostatic drug or another tissue growth inhibitor to ensure that seal 302 remains accessible.

Figure 4:
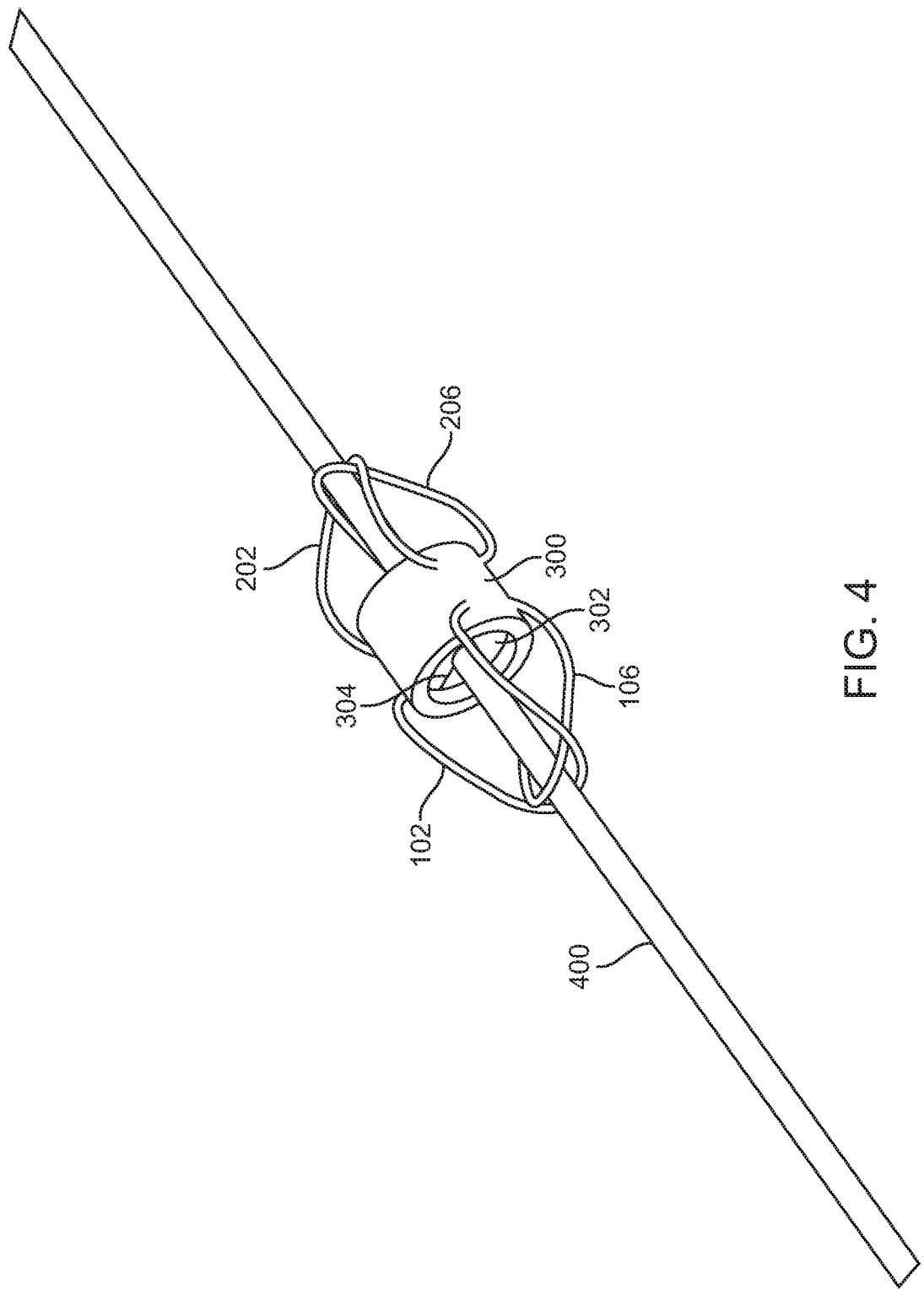
FIG. 4 illustrates the medical device attached to a guide wire, according to an embodiment.

FIG. 4 illustrates closure device 10 loaded onto guide wire 400, according to an embodiment. Closure device 10 can be loaded for delivery in many different ways. In the embodiment shown in FIG. 4, top end 202 and bottom end 206 of proximal loop 200 can be folded proximally so that the ends overlap. Guide wire 400 can be threaded such that it retains top end 202 and bottom end 206 in a folded position. Guide wire 400 can then be inserted through seal 302 of plug 300, for example through slit 304, so that a distal end of guide wire 400 is exposed on the distal side of seal 302. Top end 102 and bottom end 106 of distal loop 100 can then be folded distally in the same matter as proximal loop 200. Guide wire 400 can be threaded through the overlapped ends to secure closure device 10 onto guide wire 400. In this loaded configuration, closure device 10 can be advanced along guide wire 400 to the deployment location. In certain embodiments, guide wire 400 can be lubricated with a biocompatible lubricant to facilitate advancing closure device 10 along guide wire 400.

Figure 5:
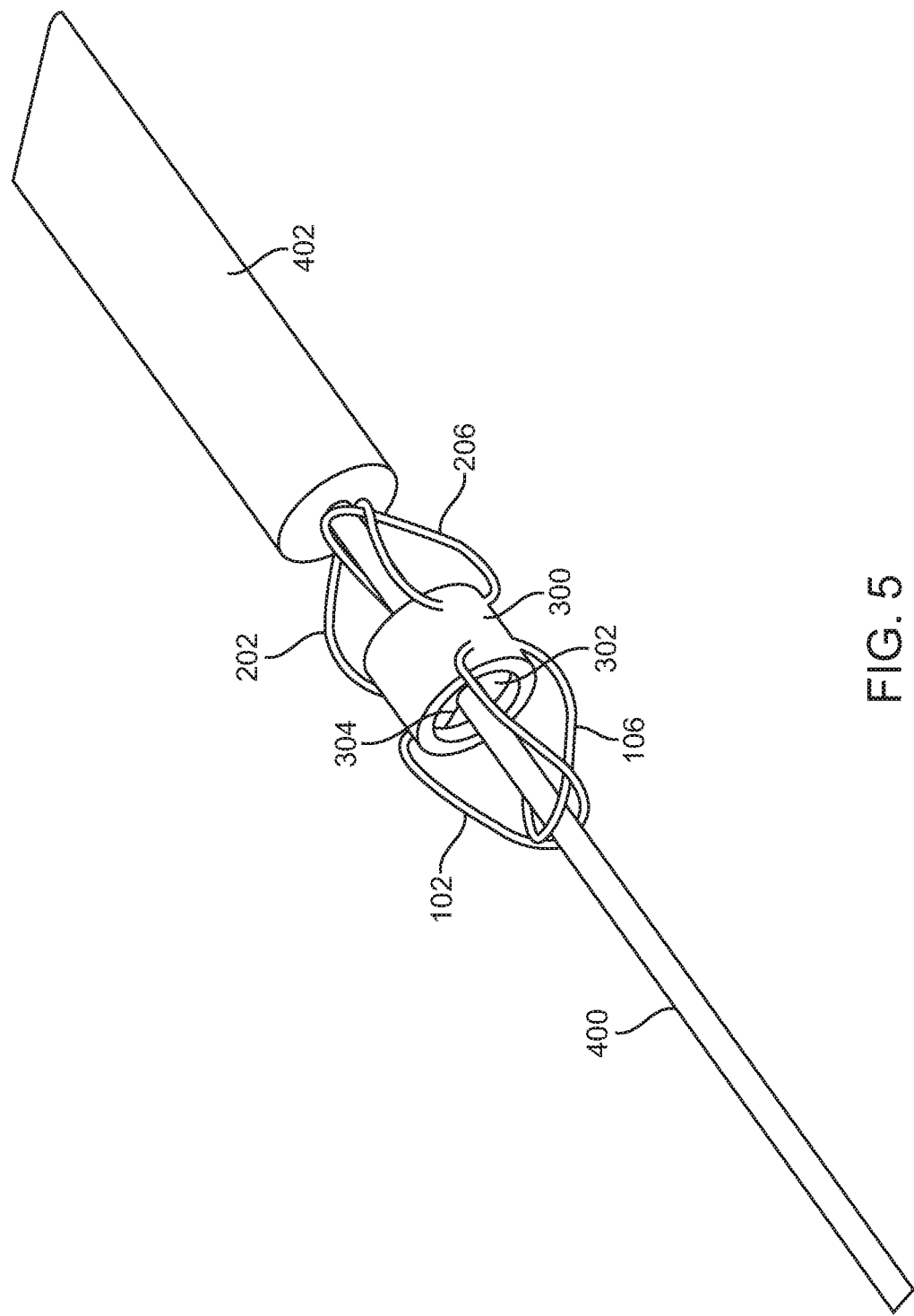
FIG. 5 illustrates the medical device attached to a guide wire along with a pushing tube, according to an embodiment.

As shown in FIG. 5, the delivery system can include pushing tube 402. In certain embodiments, pushing tube 402 can include an interior lumen such that it can slide along guide wire 400. By advancing pushing tube 402 in the distal direction, closure device 10 can be advanced along guide wire 400 to the deployment location. In certain embodiments, pushing tube 402 can include a retaining mechanism, for example, a latch or a suture, to releasably attach closure device 10 to pushing tube 402. Pushing tube 402 can also be used to brace closure device 10, so that guide wire 400 can be retracted proximally to release the ends of the loops.

Figure 6:
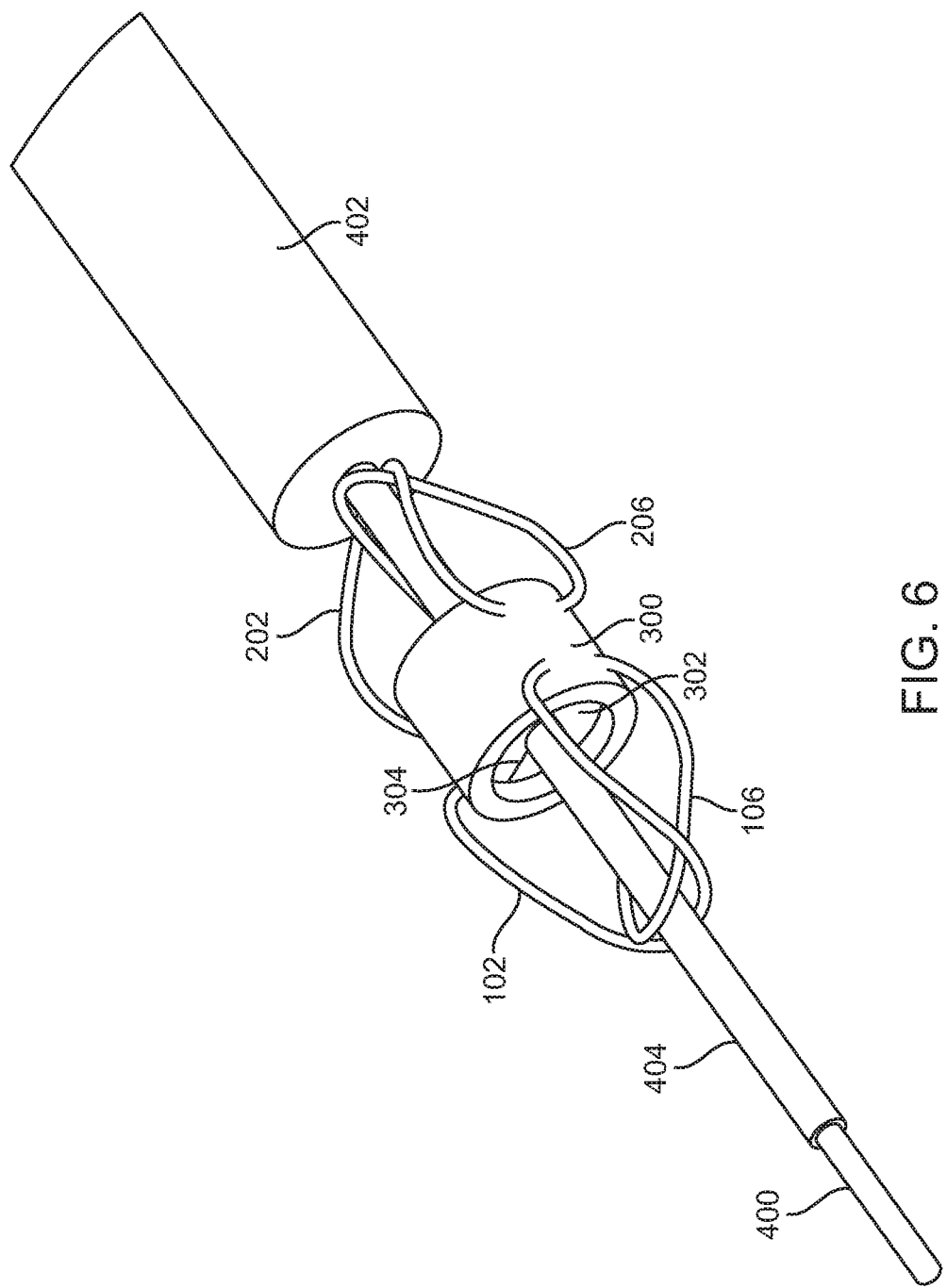
FIG. 6 illustrates the medical device attached to a retaining tube, according to an embodiment.

In certain embodiments, such as the one shown in FIG. 6, the delivery system can also include retaining tube 404. Retaining tube 404 can include an interior lumen such that it can slide along guide wire 400. Closure device 10 can be loaded onto retaining tube 404 in a manner similar to that described above with respect to the embodiment depicted in FIG. 4, where closure device 10 is loaded onto guide wire 400. In the embodiment shown in FIG. 6, pushing tube 402 can be used to push retaining tube 406 and closure device 10 along guide wire 400 to the deployment location. Guide wire 400 can then be proximally retracted prior to deployment of closure device 10. Pushing tube 402 can then be used to push closure device 10 off of retaining tube 404 to deploy closure device 10.

Figure 7A:
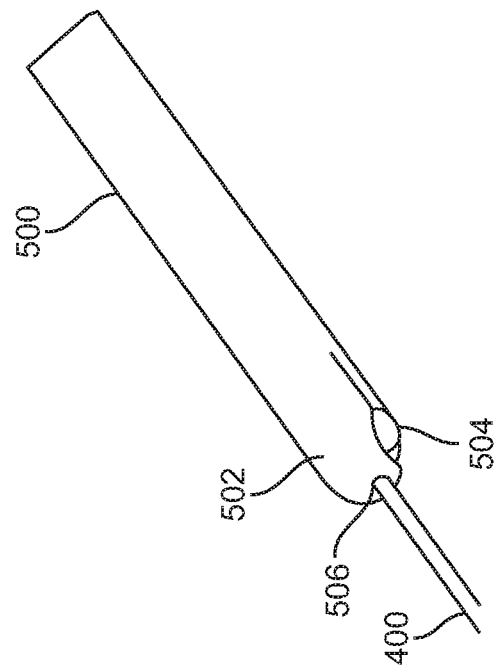
FIGS. 7A through 7O illustrate a sheath and the sheath secured to a guide wire about the medical device, according to an embodiment.
Figure 7B:
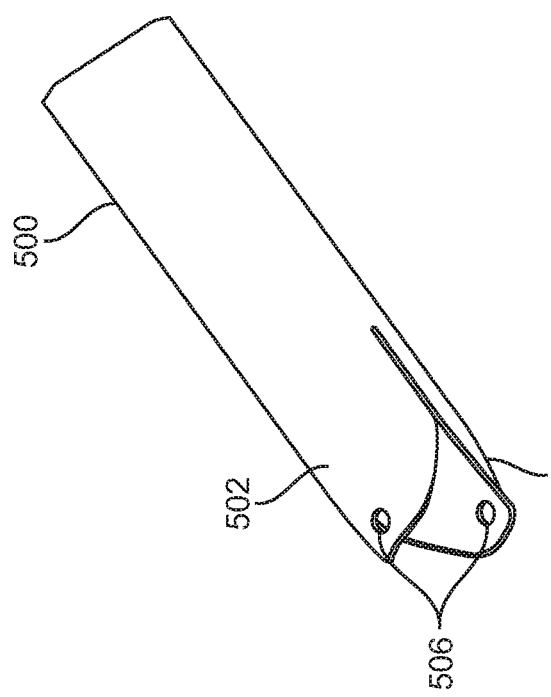
Figure 7C:
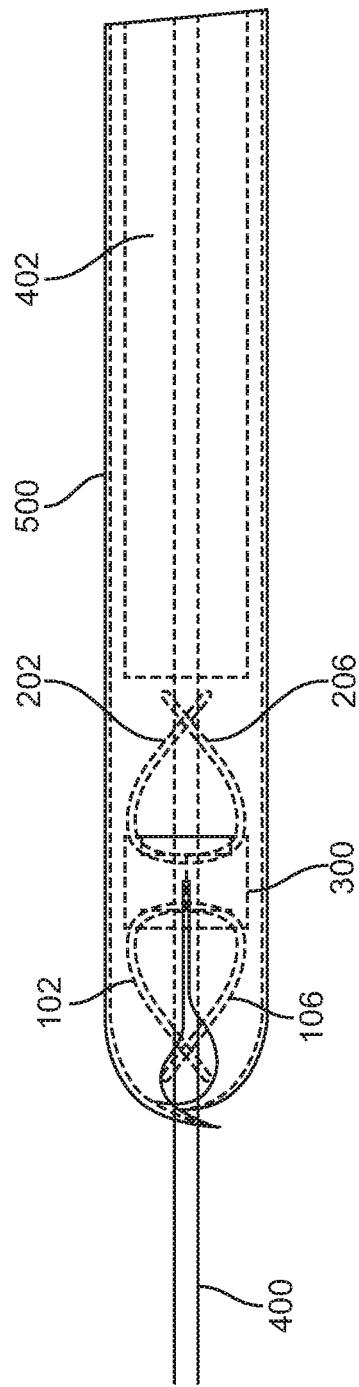

FIGS. 7A through 7C illustrate the delivery system, including sheath 500, according to an embodiment. Closure device 10 can be delivered in an exposed condition, such as illustrated in FIGS. 4 through 6, or sheath 500 can be used to protect closure device 10, as well as the inside of the vasculature, while advancing the delivery system to the deployment location. Sheath 500 can include upper leaf 502 and lower leaf 504 at a distal end of sheath 500. Holes 506 can be provided at the distal end of each leaf so that guide wire 400 can be threaded through upper leaf 502 and lower leaf 504 to close sheath 500 about closure device 10.

In certain embodiments, sheath 500 can be made of a semi-flexible, smooth material. For example, sheath 500 can be made of a material such as, but not limited to, Teflon®. The distal end of sheath 500 can be cut or formed to have two or more leaves, such as upper leaf 502 and lower leaf 504. Each leaf can have a hole 506 located near its distal tip such that when folded and held in place by retaining tube 404 or guide wire 400, sheath 500 can have a tapered tip. In certain embodiments, cinching of upper leaf 502 and lower leaf 504 can include using sutures or additional lumens as part of retaining tube 404. Multiple hole quantities and alternative hole locations within the leaves can also be used.

FIGS. 8A through 8L illustrate the delivery and implantation procedure for closure device 10 using the delivery system. The procedure would be similar for both atrial and ventricular septal defects, as well as for other anatomical apertures. By way of example, FIGS. 8A-8L will be described in relation to the delivery and implantation procedure for an ASD.

In order to deliver closure device 10, the user needs to gain percutaneous access to the heart. This can be accomplished, for example, by making an incision in the femoral artery or femoral vein, and advancing a guide wire through the vasculature to the defect location. As illustrated in FIG. 8A, guide wire 400 can be guided through defect hole 602 in heart wall 600. This can be accomplished, for example, by using a steerable or non-steerable guide catheter which can then be removed, leaving only guide wire 400 crossing defect hole 602, as illustrated in FIG. 8A.

Figure 8B:
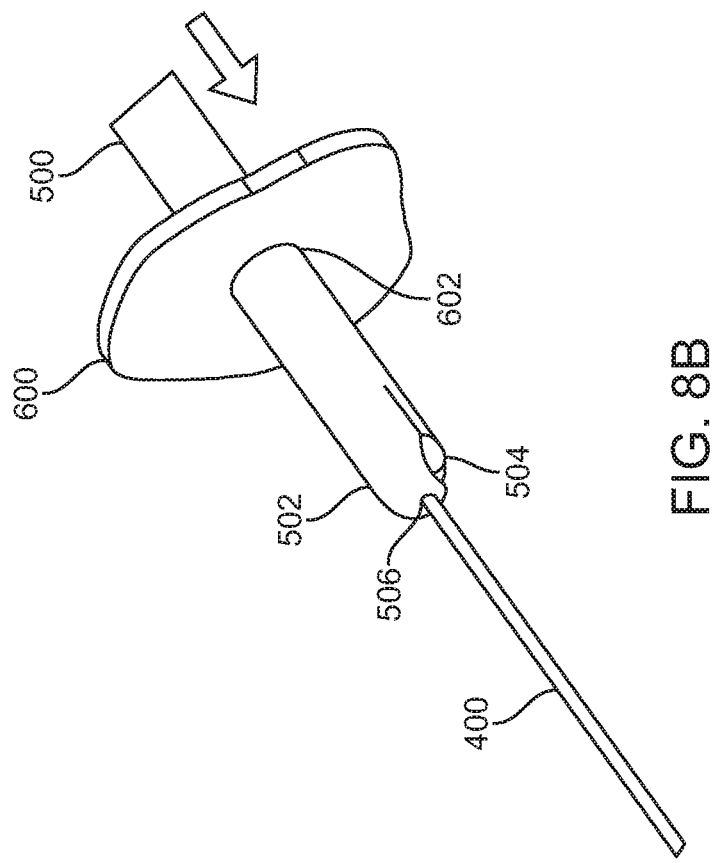
Figure 8A:
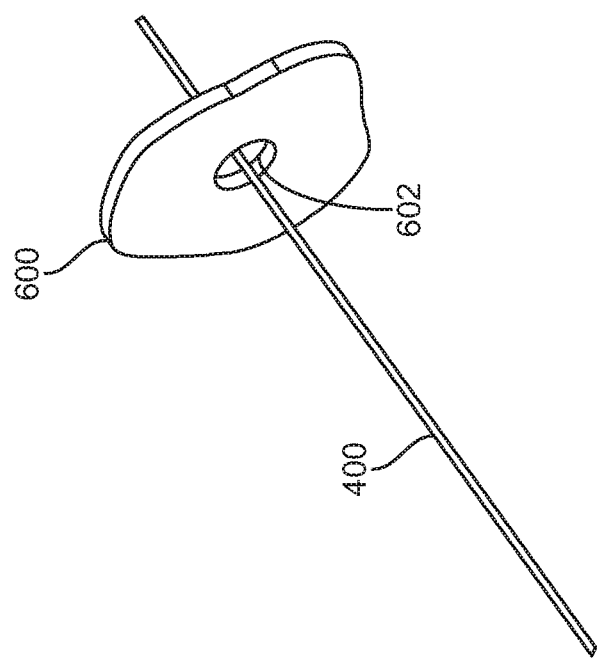

In the embodiment illustrated in FIG. 8B, closure device 10, covered by sheath 500 can be introduced along guide wire 400 and through defect hole 602 of heart wall 600. As discussed above, closure device 10 can also be inserted over guide wire 400 without sheath 500. The delivery system can be advanced through defect hole 602 such that the distal end of sheath 500, including upper leaf 502 and lower leaf 504, is located on a distal side of heart wall 600.

Figure 8D:
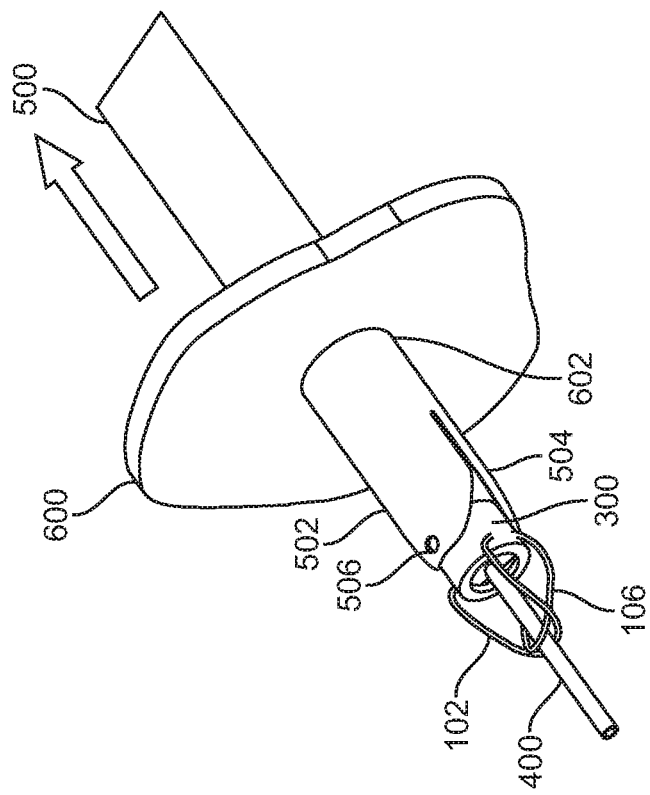
Figure 8C:
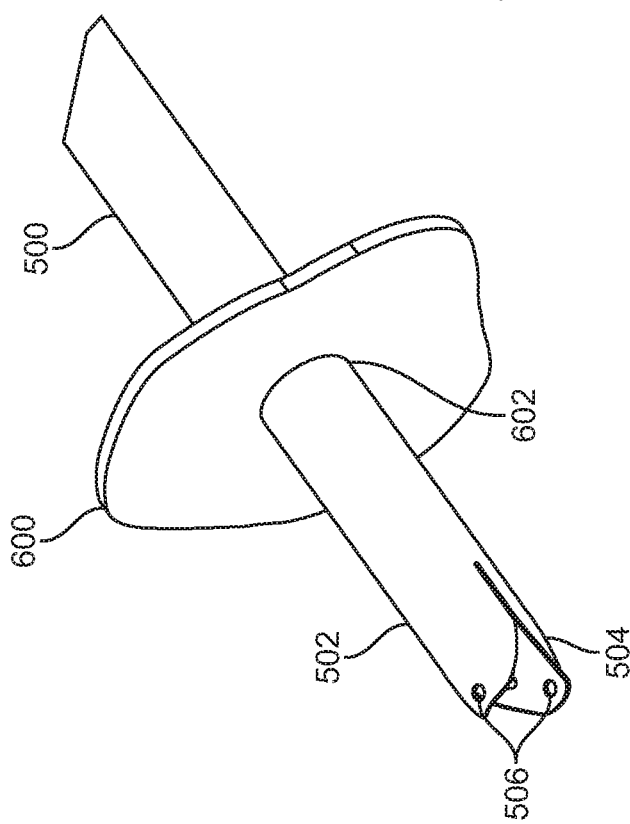

FIG. 8C illustrates the delivery system after upper leaf 502 and lower leaf 504 are disengaged from guide wire 400. In certain embodiments, this can be accomplished by advancing sheath 500 in a distal direction beyond a distal end of guide wire 400. In certain embodiments, this can alternatively be accomplished by retracting guide wire 400 in a proximal direction. By disengaging guide wire 400 from upper leaf 502 and lower leaf 504, the distal end of sheath 500 can form an opening.

As shown in FIG. 8D, sheath 500 can be retracted in the proximal direction, as indicated by the arrow. This can expose at least a portion of closure device 10, which is still mounted on guide wire 400.

As shown in FIG. 8E, guide wire 400 can be further retracted in the proximal direction, thus releasing top end 102 and bottom end 106 of distal loop 100 from guide wire 400. This can allow top end 102 and bottom end 106 to return to their preset biased shape. FIG. 8F illustrates this step of the deployment sequence in a side view. As shown, top end 102 and bottom end 106 of distal loop 100 are released from guide wire 400 and open outside of sheath 500. Sheath 500 can still cover top end 202 and bottom end 206 of proximal loop 200, which are still threaded onto guide wire 400, such that they remain in their delivery configuration.

As illustrated in FIG. 8G, the entire delivery system can be retracted in the proximal direction until top end 102 and bottom end 106 of distal loop 100 contact heart wall 600. As shown in the side view of FIG. 8H, distal loop 100 can contact heart wall 600, while top end 202 and bottom end 206 of proximal loop 200 are still threaded onto guide wire 400 and constrained within sheath 500. In certain embodiments, the contact of distal loop 100 against heart wall 600 can be detected by echo, fluoroscopy, tactile feedback or other methods. To prevent closure device 10 from slipping off the end of guide wire 400, in certain embodiments, a tether can be employed through additional lumens or through the center lumen of pushing tube 402 to retain closure device 10 on guide wire 400. In addition, a tether can provide a method of recapture if a user wants to remove closure device 10 after placement. Generally, seal 302 and top end 202 and bottom end 206 of proximal loop 200 can provide enough friction with guide wire 400 to provide tactile feedback and prevent closure device 10 from slipping off of guide wire 400.

FIG. 8I illustrates retraction of sheath 500 further in the proximal direction as indicated by the arrow. As shown in the side view of FIG. 8J, top end 202 and bottom end 206 of proximal loop 200 are now exposed, but still attached to guide wire 400. As shown in FIGS. 8K and 8L, guide wire 400 can be retracted further in the proximal direction, such that guide wire 400 no longer extends through slit 304 of seal 302. Further retraction of guide wire 400 in the proximal direction causes top end 202 and bottom end 206 of proximal loop 200 to be released from guide wire 400. This allows top end 202 and bottom end 206 to return to their unconstrained, preset configuration and engage heart wall 600. At this point, closure device 10 is completely deployed and the delivery system can be retracted and removed from the body.

Figure 9:
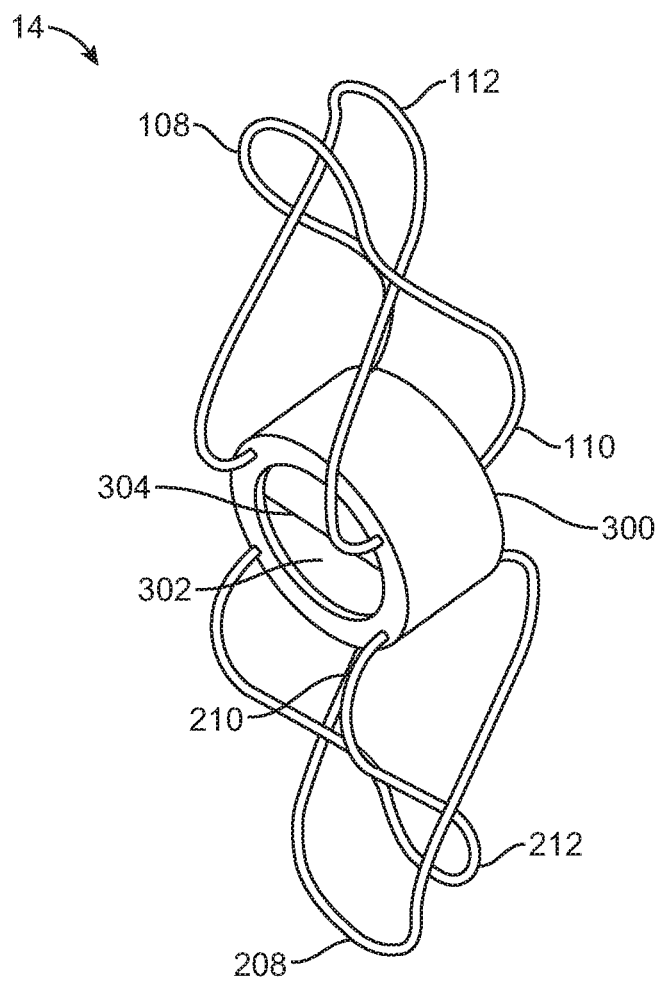
FIG. 9 illustrates an alternative embodiment of the medical device.

FIG. 9 illustrates an alternative embodiment of closure device 14. This embodiment includes an upper and a lower loop, as opposed to a distal and proximal loop. In certain embodiments, the upper loop can be sized and shaped such that distal portion 112 can fit within proximal portion 108, and the bottom loop can be sized and shaped such that distal portion 212 can fit within proximal portion 208. In certain embodiments, proximal portions 108 and 208 can be sized and shaped to fit within distal portions 112 and 212. In the embodiment shown in FIG. 9, middle portions 110 and 210 extend through plug 300 between an interior and exterior surface of plug 300 along an axis parallel to a longitudinal axis of plug 300. In certain embodiments, plug 300 and seal 302 can be composed of a compressible material such that the entire closure device 14 can be compressed and loaded into a sheath with a smaller diameter in comparison to embodiments where plug 300 is rigid or semi-rigid. However, it should be noted that the embodiment of FIG. 9 can also include a rigid or semi-rigid plug. The compressible plug and seal can also be used in the other embodiments described herein. Using a compressible material for plug 300 can allow a single sized closure device 14 to be used for any anatomical aperture size or shape because plug 300 can expand within the aperture after deployment.

Figures 10A, 10B:
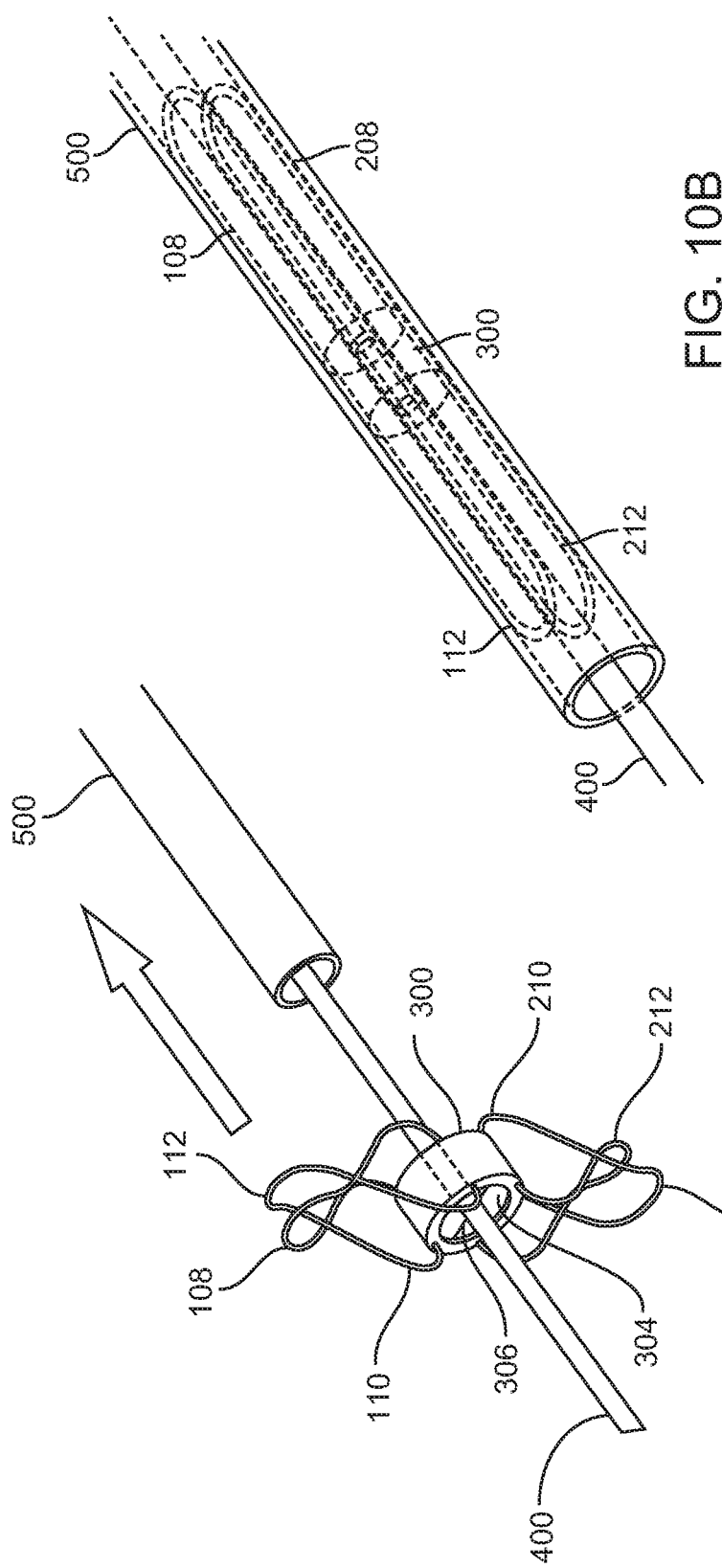
FIGS. 10A and 10B illustrate the medical device of FIG. 9 loaded onto a guide wire and within a sheath.

FIGS. 10A and 10B illustrate the embodiment of FIG. 9 loaded onto guide wire 400 and into sheath 500, respectively. Proximal portions 108 and 208 and distal portions 112 and 212 can be loaded onto guide wire 400 in a manner similar to other embodiments, by folding them down and threading guide wire 400 through them. Alternatively, guide wire 400 can extend through slit 304 of seal 302 without threading through either loop. Proximal portions 108 and 208 can be folded proximally and loaded into sheath 500. Plug 300 can be compressed and loaded into sheath 500, and then distal portions 112 and 212 can be folded in a distal direction and loaded into sheath 500 by sliding the closure device in a proximal direction or advancing sheath 500 in a distal direction. FIG. 10B illustrates closure device 14 when loaded into sheath 500.

Methods of delivering a medical device for closing an anatomical aperture are also disclosed. References to the figures are meant by way of example, and are not meant to be limiting. In certain embodiments, an entry point can be created, such as by making an incision in the femoral artery or femoral vein, and an introducer catheter can be used to facilitate insertion of the delivery system. Guide wire 400 can be advanced through the body lumen to a deployment location. Closure device 10 can be loaded onto guide wire 400, before or after guide wire 400 is inserted into the body lumen, and closure device 10 itself can then be inserted into the body lumen. In certain embodiments, pushing tube 402 can be used to advance closure device 10 along guide wire 400 to the deployment location. Closure device 10 can then be deployed by retracting guide wire 400 in a proximal direction, or by pushing closure device 10 off of guide wire 400 in a distal direction. Guide wire 400 and pushing tube 402 can then be removed from the body lumen. In certain embodiments, pushing tube 402 can be used to brace closure device 10 while retracting guide wire 400 in the proximal direction.

In certain embodiments, closure device 10 can be delivered by first loading closure device 10 onto guide wire 400. This can be accomplished by folding top end 202 and bottom end 206 of proximal loop 200 in a proximal direction and threading guide wire 400 under bottom end 206 and over top end 202, or vice versa. Guide wire 400 can then be advanced through seal 302 of plug 300, for example, through slit 304. Top end 102 and bottom end 106 of distal loop 100 can then be folded in a distal direction, and guide wire 400 can be threaded under bottom end 106 and over top end 102, or vice versa, in order to secure closure device 10 onto guide wire 400. In certain embodiments, retaining tube 404 can be included about guide wire 400 and closure device 10 can be loaded onto retaining tube 404 in a similar manner.

Guide wire 400 can be advanced through a patient's vasculature to a deployment location. Closure device 10 can then be advanced along guide wire 400, such as by pushing it with pushing tube 402 in a distal direction along guide wire 400. In certain embodiments, closure device 10 and pushing tube 402 can be covered by sheath 500. Guide wire 400 can be threaded through holes 506 in upper leaf 502 and lower leaf 504 of sheath 500 to close a distal end of sheath 500. The delivery system can be advanced along guide wire 400 until a distal end of sheath 500 passes through defect hole 602 of heart wall 600. Guide wire 400 can be retracted in the proximal direction, or sheath 500 can be advanced in the distal direction beyond a distal end of guide wire 400, to release upper leaf 502 and lower leaf 504 from guide wire 400. Sheath 500 can then be retracted in the proximal direction to expose top end 102 and bottom end 106 of distal loop 100. Guide wire 400 can then be further retracted in the proximal direction to release top end 102 and bottom end 106 of distal loop 100 from guide wire 400, allowing distal loop 100 to spring back to its unconstrained, preset configuration.

Once distal loop 100 is released, the entire delivery system can be retracted in the proximal direction until top end 102 and bottom end 106 of distal loop 100 contact a distal side of heart wall 600. Sheath 500 can then be retracted further in the distal direction to expose top end 202 and bottom end 206 of proximal loop 200. Guide wire 400 can then be retracted further in the proximal direction to release top end 202 and bottom end 206 of proximal loop 200, thus allowing proximal loop 200 to spring back to its unconstrained, preset configuration and contact a proximal side of heart wall 600. The force of each loop against heart wall 600 can secure closure device 10 within defect hole 602. The delivery system can then be retracted from the body and the entry point can be closed, for example, with sutures.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed:

1. A method of closing an anatomical aperture comprising:
   providing a delivery system for delivering a medical device for closing an anatomical aperture, the delivery system comprising a guide wire, a pushing tube, and a medical device comprising a plug body having a proximal end, a distal end, and an interior lumen along a longitudinal axis of the plug body, a seal located within the interior lumen, and a first pair of arms extending from the proximal end of the plug body and a second pair of arms extending from the distal end of the plug body, wherein each of the arms of the first and second pairs of arms comprises a loop;
   loading the medical device onto the guide wire, wherein loading the medical device onto the guide wire includes folding each of the loops of the arms of the first pair in a proximal direction so that the loops of the arms of the first pair overlap, folding each of the loops of the arms of the second pair in a distal direction so that the loops of the arms of the second pair overlap, and threading the guide wire through each of the loops of the arms of the first pair, through the seal located within the interior lumen of the plug body, and through each of the loops of the arms of the second pair;
   inserting the delivery system into a body lumen;
   advancing the guide wire through the body lumen to a deployment location within the anatomical aperture;
   pushing the medical device along the guide wire with the pushing tube through the body lumen to the deployment location; and
   deploying the plug body of the medical device within the anatomical aperture such that the first pair of arms secure against tissue at the proximal end of the plug body and the second pair of arms secure against tissue at the distal end of the plug body.

2. The method of claim 1, further comprising removing the guide wire and pushing tube from the body lumen after deploying the medical device.

3. The method of claim 1, wherein deploying the plug body of the medical device comprises bracing the medical device with the pushing tube and retracting the guide wire in a proximal direction.

4. The method of claim 1, wherein the delivery system further comprises a sheath, wherein a distal end of the sheath comprises an upper leaf and a lower leaf, each having an aperture through which the guide wire can pass to close the distal end of the sheath, and wherein deploying the medical device comprises:
   retracting the guide wire proximally to open the distal end of the sheath;
   retracting the sheath proximally and further retracting the guide wire proximally to release the loops of the arms of the second pair on the distal end of the plug body;
   to engage the loops of the arms of the second pair with tissue of a heart wall; and
   further retracting the sheath and the guide wire proximally to release the loops of the arms of the first pair on the proximal end of the plug body to engage the loops of the arms of the first pair with tissue of the heart wall.

5. The method of claim 1, wherein the anatomical aperture is an opening in a heart wall.

6. The method of claim 5, wherein the seal comprises a pierce-able septum that is configured to allow a medical tool to pierce the seal and then self-reseal once the medical tool is removed.

7. The method of claim 6, wherein the medical tool is a catheter.

8. The method of claim 7, wherein the opening in the heart wall is surgically created between a right atrium and a left atrium for percutaneous access to a left side of a heart for mitral valve repair.

9. The method of claim 8, wherein the seal is coated with a cytostatic agent for preventing tissue growth over the seal to allow for re-access to the left atrium at a later time.

10. A method of closing an opening in a heart wall comprising:
    loading a medical device for closing an opening in a heart wall onto a delivery system, the medical device comprising a plug body having a proximal end, a distal end, and an interior lumen along a longitudinal axis of the plug body, a seal located within the interior lumen, and a first pair of arms extending from the proximal end of the plug body and a second pair of arms extending from the distal end of the plug body;
    advancing the delivery system through a vasculature to a deployment location at the opening in the heart wall; and
    implanting the plug body of the medical device within the opening such that the first pair of arms secure against tissue at the proximal end of the plug body and the second pair of arms secure against tissue at the distal end of the plug body;
    advancing a medical tool through the vasculature after the step of implanting the plug body;
    piercing the seal of the implanted medical device with the medical tool;
    advancing the medical tool through the seal of the implanted medical device; and
    using the medical tool to repair or replace a mitral valve of the heart.

11. The method of claim 10, wherein the opening in the heart wall is surgically created between a right atrium and a left atrium for percutaneous access to a left side of a heart for mitral valve repair.

12. The method of claim 11, wherein the seal comprises a pierce-able septum that is configured to allow the medical tool to pierce the seal and then self-reseal once the medical tool is removed.

13. The method of claim 12, wherein the medical tool is a catheter.

14. The method of claim 11, wherein the medical tool is a catheter and the seal is a hemostatic seal that permits access by the catheter to the left atrium through the implanted medical device, after the opening is surgically created.

15. The method of claim 11, wherein the delivery system comprises a guide wire, wherein each of the arms of the first and second pairs of arms comprises a loop, and wherein loading the medical device onto the delivery system comprises:
- folding each of the loops of the arms of the first pair in a proximal direction;
- folding each of the loops of the arms of the second pair in a distal direction; and
- threading the guide wire through each of the loops of the arms of the first pair, through the seal located within the interior lumen of the plug body, and through each of the loops of the arms of the second pair.

16. The method of claim 15, wherein implanting the plug body of the medical device comprises:
- retracting the guide wire proximally to release the loops of the arms of the second pair on the distal end of the plug body to engage the loops of the arms of the second pair with tissue of the left atrium; and
- further retracting the guide wire proximally to release the loops of the arms of the first pair on the proximal end of the plug body to engage the loops of the arms of the first pair with tissue of the right atrium.

17. A method of closing an opening in a heart wall comprising:
- surgically creating an opening in a heart wall between a right atrium and a left atrium;
- loading a medical device for closing the opening in the heart wall onto a delivery system, the medical device comprising a plug body having a proximal end, a distal end, and an interior lumen along a longitudinal axis of the plug body, a hemostatic seal located within the interior lumen, and a first pair of arms extending from the proximal end of the plug body and a second pair of arms extending from the distal end of the plug body;
- advancing the delivery system through a vasculature to a deployment location at the opening in the heart wall; and
- implanting the plug body of the medical device within the opening such that the first pair of arms secure against tissue at the proximal end of the plug body and the second pair of arms secure against tissue at the distal end of the plug body;
- advancing a catheter through the vasculature to the implanted medical device after the step of implanting the plug body;
- advancing the catheter through the hemostatic seal of the implanted medical device to access the left atrium through the implanted medical device; and
- using the catheter to repair or replace a mitral valve of the heart.

18. The method of claim 17, wherein the hemostatic seal is coated with a cytostatic agent for preventing tissue growth over the seal.

19. The method of claim 17, wherein the hemostatic seal comprises a pierce-able septum that is configured to allow the catheter to pierce the seal and then self-reseal once the catheter is removed.

* * * * *